United States Patent [19]

Hellberg

[11] 4,209,264
[45] Jun. 24, 1980

[54] SLIDING BLOCK SUPPORT
[75] Inventor: Arne Hellberg, Gråbo, Sweden
[73] Assignee: Hellberg Protection AB, Sweden
[21] Appl. No.: 30,821
[22] Filed: Apr. 17, 1979
[30] Foreign Application Priority Data
   May 29, 1978 [SE] Sweden ............................ 7806104
[51] Int. Cl.² ............................................ F16B 2/02
[52] U.S. Cl. ...................................... 403/80; 2/209;
                                                         179/156 R
[58] Field of Search ................. 403/80, 59, 104, 341;
            179/182 R, 182 A; 248/295 R, 298, 299;
                                 128/151, 152; 2/209 R, 423

[56]  References Cited
      U.S. PATENT DOCUMENTS

| | | | |
|---|---|---|---|
| 614,261 | 11/1898 | Dickinson | 403/59 |
| 2,149,341 | 3/1939 | Harrison | 179/156 R |
| 2,689,909 | 9/1954 | Dazley | 248/299 X |
| 3,461,463 | 8/1969 | Beguin | 2/423 |
| 3,505,684 | 4/1970 | Hutchinson et al. | 2/209 |

*Primary Examiner*—Wayne L. Shedd
*Attorney, Agent, or Firm*—Holman & Stern

[57] ABSTRACT

A sliding block for adjustably mounting e.g. an ear cup at a protective helmet or a head clamp having a U-shaped carrier includes a base member and a channel-shaped cover. The base member includes a prismatic head and a shaft projecting therefrom, and a passage extends through the head and the shaft. Grooves are provided at two mutually opposite sides at the head for receiving the shanks of the carrier. In mounted position the cover will enclose the head and lock the shanks in the grooves, however permitting a sliding movement of the block along the carrier.

The cover has an internal projection snapping into the mouth of the passage at the head, and the opposite mouth of the passage is provided with tongues for engaging a stud on the ear cup.

2 Claims, 5 Drawing Figures

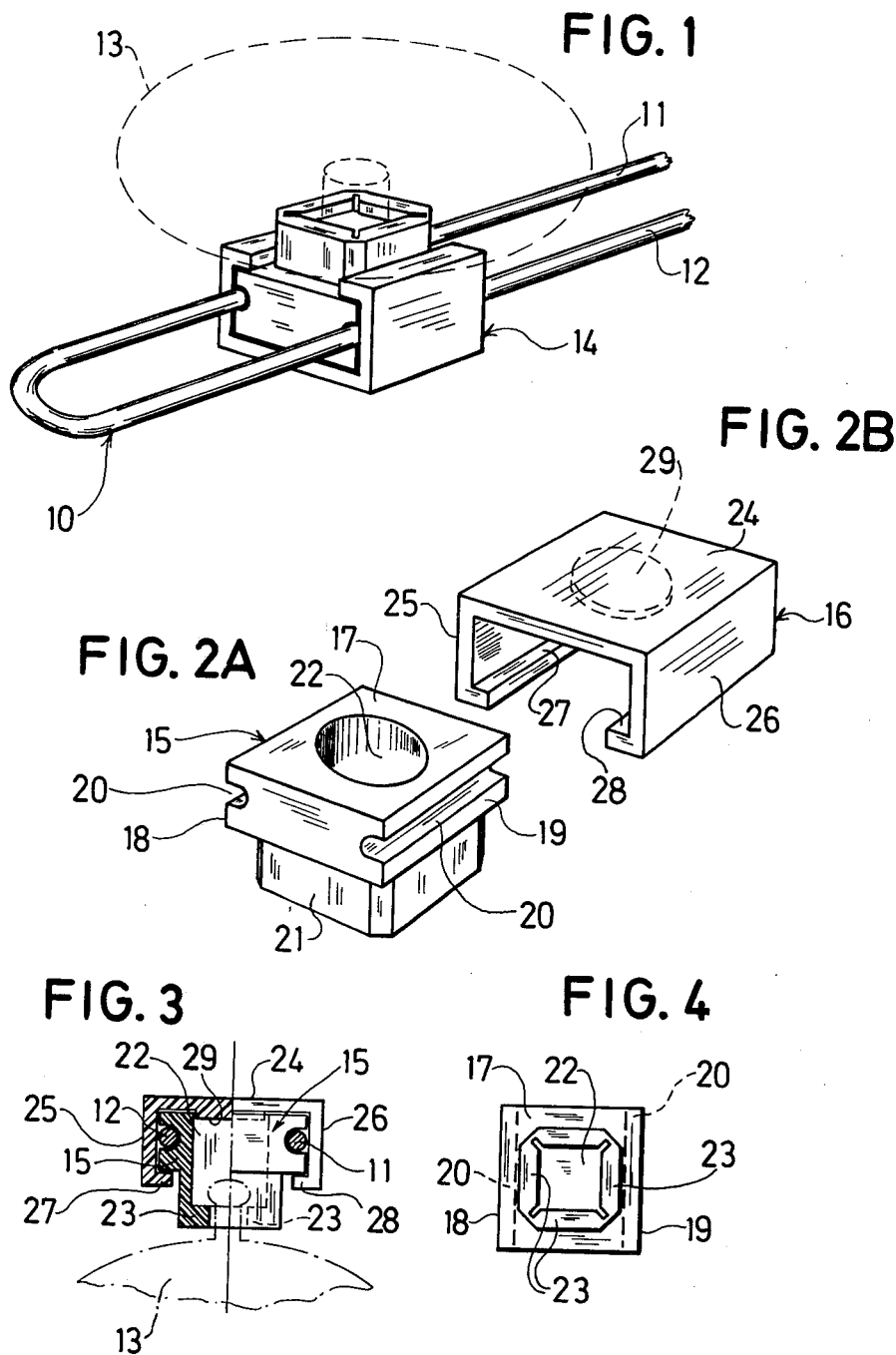

4,209,264

SLIDING BLOCK SUPPORT

BACKGROUND OF THE INVENTION

The present invention refers to a sliding block adapted to be mounted at a U-formed carrier for supporting a component, so as to be movable along the carrier. The invention is of special importance to ear protectors, where the ear cups are mounted so they may be displaced lengthwise in relation to U-shaped carriers, as well as being rotatable in relation thereto. A pair of such carriers may form part of a head clamp, but may also be fitted individually at a protective helmet, on which occasion the carriers are rotatable in relation thereto.

In both embodiments the shanks of the U will be firmly attached to a base—the head clamp or a fitting at the helmet—which means that the sliding block intended to carry the ear cup must be fitted at an early stage of the mounting operation. This is especially difficult when the cups are to be fitted at a helmet, where the carrier is manufactured from resilient material, and the ends of the shanks are formed into springs mounted in the fitting to be attached to the helmet. With certain known slide blocks parallel passages for the shanks have been provided, which means that such sliding blocks must be fitted when the shanks are still straight.

With known designs it has furthermore been impossible to substitute a damaged sliding block.

SUMMARY OF THE INVENTION

The aim of the present invention is to propose a sliding block, which may easily be fitted even when the mounting of the carrier has been terminated, and which makes possible a substitution of a damaged block.

A sliding block according to the invention comprises two parts, a base member including a head and a shaft projecting therefrom, as well as a cover adapted to enclose the head. The characterizing features will be evident from claim 1.

The head and the shaft are preferably formed with an axially directed through-passage, the openings of which at the distal end of the shaft being provided with inwardly directed tongues adapted to engage a stud-formed portion of the component. The cover is provided with an internal projection suited to snap into the opposite opening of the passage.

BRIEF DESCRIPTION OF THE DRAWING

FIG. 1 shows a detail of a carrier having a sliding block suited to support an ear cup mounted thereon, FIGS. 2a and b show perspective views of a base member and a cover, separate from each other, FIG. 3 shows an end view of a slide block mounted upon a carrier, and FIG. 4 shows the base member, as viewed from the cover end.

DESCRIPTION OF A PREFERRED EMBODIMENT

FIG. 1 shows the end portion of a carrier 10 manufactured of spring steel wire, bent into U-form. The shanks 11 and 12 include parallel straight portions extending away from the base of the U. The distal ends of the shanks are in arbitrary manner, not shown in the drawing, formed to suit mounting at a head clamp or at a fitting for attachment to a protective helmet.

An ear cup 13, indicated in broken lines, is rotatably mounted on a sliding block 14, which is axially displaceable along the straight portions of the shanks 11 and 12.

The sliding block 14 comprises a base member 15 and a cover 16. The base member 15 includes a head 17, which here is formed as a plane plate defined by two parallel side-walls 18, 19. Those are arranged at a mutual distance mainly corresponding to the distance between shanks 11 and 12. Each side wall is provided with a longitudinally extending groove 20, adapted to receive one shank.

A shaft 2 projects from head 17 and is narrower than the distance between side walls 18, 19. A passage 22 extends right through the head and the shaft in the axial direction of the latter. The opening of the passage at its end remote from the head 17 is provided with a number of tongues 23, projecting into the passage. These tongues are adapted to retain the head of a stud or button (denoted in broken lines in FIG. 3) at ear cup 13. Such a stud may, in a well known manner, be forced into the passage, and will then be retained by tongues 23. The arrangement permits the ear cup to be rotated in relation to the sliding block, and thus also in relation to carrier 10.

The head 17, with the open grooves 20 can easily be fitted between shanks 11 and 12, by an elastic deformation of the latter, even when the ends of the shanks have been permanently fitted into a head clamp or a helmet mounting.

The cover 16 ensures retention of the base member at the carrier. The cover has, as is best evident from FIGS. 2b and 3, a channel shaped cross section, with a top pane 24 having the same internal breadth as the distance between side walls 18, 19 of the head. Two side walls 25, 26 project from the top pane 24, and have the same depth as the thickness of the head 17. Each side wall is terminated by an inwardly directed flange 27, 28.

The top pane 24 is, at its inward face, provided with a projection 29, mating with the opening of passage 22 in the upper face of the head.

The cover 16 is manufactured of a resilient material, and it may be slid over the head in the longitudinal direction of the carrier shanks. When the cover reaches its intended position, projection 29 snaps into passage 22, and will then prevent relative movements between the head and the cover. The completed sliding block will be securely mounted on the carrier, but may be displaced in the longitudinal direction thereof. By selecting the material and the dimensions properly it is possible to obtain a desirable degree of resistance against unintended displacement, so the sliding block will be frictionally retained in its adjusted position.

What I claim is:

1. A sliding block for movably supporting a component on a U-shaped carrier having parallel shanks and comprising
    a base member having a head and a shaft projecting therefrom, said head being including a least two parallel, laterally spaced side walls arranged at a distance mainly corresponding to the distance between the shanks of said U-shaped carrier,
    a groove in each of said side walls frictionally receiving one of said shanks, and
    a channel-shaped cover which grippingly encloses said head and said side walls whereby said block is frictionally supported by said carrier.

2. The sliding block according to claim 1, in which said head and said shaft are formed with an axially directed through-passage having a first opening in the distal end of the shaft and a second opening in the head, said first opening being provided with inwardly directed tongues adapted to engage a projecting part of the component, and said cover being provided with an internal projection sized to snap into said second opening.

* * * * *